United States Patent [19]

Jamison et al.

[11] Patent Number: 4,567,764
[45] Date of Patent: Feb. 4, 1986

[54] DETECTION OF CLAD DISBOND

[75] Inventors: Thomas D. Jamison, Fort Oglethorpe, Ga.; Frank T. Radcliff, Chattanooga, Tenn.

[73] Assignee: Combustion Engineering, Inc., Windsor, Conn.

[21] Appl. No.: 565,509

[22] Filed: Dec. 27, 1983

[51] Int. Cl.$^4$ ............................................. G01N 29/04
[52] U.S. Cl. ........................................ 73/588; 73/582; 73/600; 73/611
[58] Field of Search ................. 73/579, 582, 588, 597, 73/599, 600, 611; 367/47, 29, 66, 67

[56] References Cited

U.S. PATENT DOCUMENTS

| | | | |
|---|---|---|---|
| 3,580,056 | 5/1971 | Warner | 73/579 |
| 4,184,373 | 1/1980 | Evans et al. | 73/588 |
| 4,202,515 | 5/1980 | Meyer | 73/599 |
| 4,475,398 | 10/1984 | Tjornehoj et al. | 73/599 |
| 4,479,386 | 10/1984 | Beggs et al. | 73/582 |

Primary Examiner—Howard A. Birmiel
Attorney, Agent, or Firm—David L. Smith

[57] ABSTRACT

A method and apparatus for detecting disbond in laminar workpieces. Energy is transmitted to a workpiece (8) by repetitive impacts. A transducer (12) converts energy emitted from the workpiece (8) to an electrical signal. The energy emitted in response to each of the repetitive impacts is analyzed. After filtering out the DC component (20) and amplifying the signal (30) the maximum amplitude of the energy from each impact is selected (50) and passed to a sample and hold circuit (60). The piecewise linear output of the sample and hold circuit (60) is passed through a low pass active filter (70) prior to recording on a strip chart recorder. The strip chart record is analyzed to ascertain areas of the workpiece (8) having defective clad bonding (7).

9 Claims, 7 Drawing Figures

DETECTION OF CLAD DISBOND

BACKGROUND OF THE INVENTION

This invention relates to nondestructive testing and in particular to a method and apparatus for inspecting laminar structures for defects in bonding between layers.

Coal is pulverized in a mill by passing the coal between a rotating bowl and a plurality of pulverizer rolls. The pulverizer rolls experience erosion as the coal is crushed and thus require a surface that is fabricated of wear resistant material. Rather than fabricate the entire roll of wear resistant material, the body is fabricated of gray iron and one or more layers of a clad material, chosen for its particular wear resistant property, are applied over the base material of gray iron. The clad construction is more economical than fabricating the entire roll from the wear resistant material. The clad material is often applied to the base material in the form of a hard facing or layer of weld material applied to the bodies outer surface. This method of construction has application both in the manufacture of new pulverizer rolls as disclosed in U.S. Pat. No. 4,389,767 and in the remanufacture of pulverizer rolls that have eroded in operation.

A problem has been encountered in using the laminar construction rolls. Due to defective bonding between layers of clad material or between a layer of clad material and the body of a pulverizer roll, the clad material in the region of the defective bond separates from the roll surface leaving a corresponding recessed area which reduces the efficiency of the pulverizer.

Therefore, a need exists for a simple, reliable nondestructive method and apparatus for detecting the presence and location of disbond flaws between clad layers or between the clad layer and the body of the pulverizer roll. Such a nondestructive method and apparatus would be useful to inspect pulverizer rolls of laminar construction as part of a manufacturing process or as part of a field inspection of equipment during routine maintenance.

SUMMARY OF THE INVENTION

The present invention provides a simple, reliable nondestructive method and apparatus for detecting the presence and location of disbond flaws between clad layers or between a clad layer and the base material of a laminar construction workpiece.

In accordance with the present invention, a series of approximately equally spaced scan lines is established on the laminar workpiece. The workpiece is energized by repetitive physical impact. The acoustic energy emitted by the workpiece in response to the repetitive physical impacts is converted to a representative electrical signal by a transducer. The representative signal of each physical impact is analyzed by passing the signal through a peak detecting circuit. The peak amplitude of the representative signal of each physical impact or a sequence of physical impacts is passed to a sample and hold circuit which maintains the last received peak until a subsequent peak is received resulting in a piecewise linear output. The piecewise linear output is passed through a filtering circuit to smooth the piecewise linear output of the sample and hold circuit resulting in a smooth representation of the peak amplitudes of the acoustic energy emitted from the workpiece. A threshhold value of the smooth representation of the peak amplitude is determined above which is considered a defect in bonding.

DESCRIPTION OF THE PREFERRED EMBODIMENT

Figure 1:
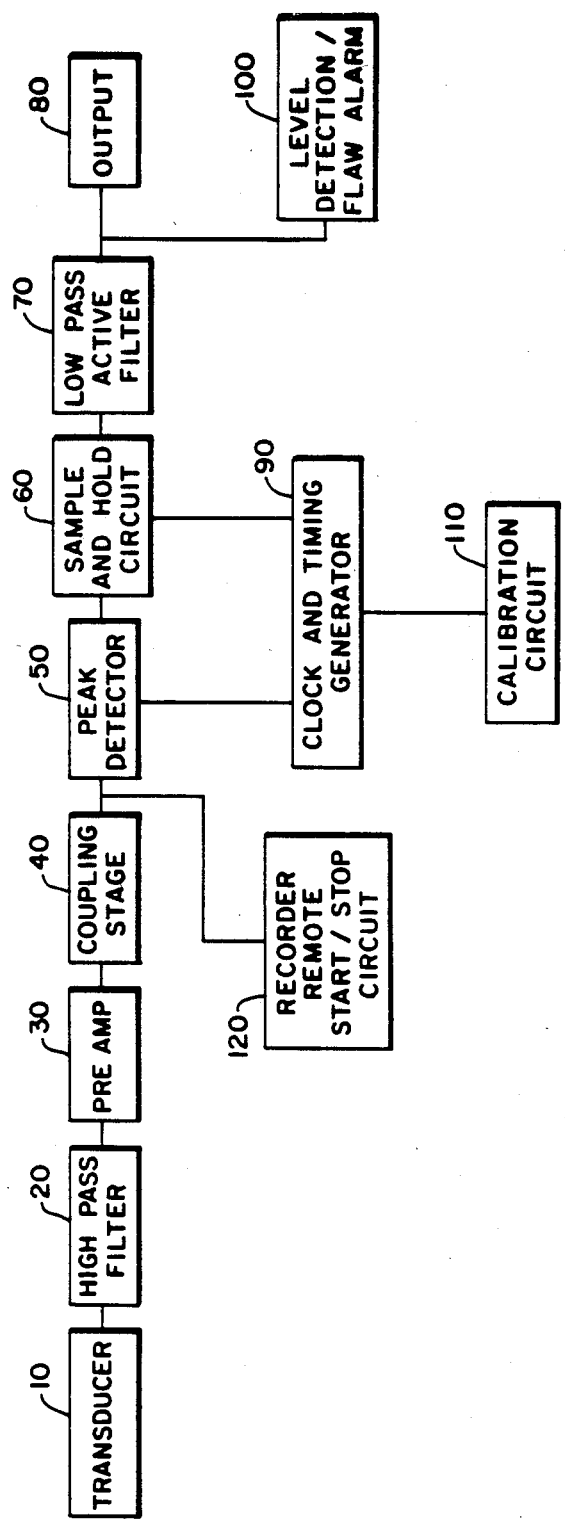
FIG. 1 is a block diagram of a clad disbond apparatus in accordance with the present invention.

Referring to the drawing, initially to FIG. 1, there is depicted an apparatus for inspecting laminar workpieces for defects in bonding between layers constructed in accordance with the present invention. Transducer 10 receives the acoustic energy emitted from the workpiece under test and produces a corresponding electrical output signal representative of the acoustic input signal. The representative electrical signal produced by transducer 10 is passed through high pass filter 20 to filter out any direct current component in the signal. The filter signal is then passed to preamplifier 30 for preliminary amplification and then passed through coupling stage 40 to block any direct current component introduced in preamplifier 30. The signal passed by coupling stage 40 is received by peak detector 50 which tracks the input signal and maintains as its output a signal representative of the maximum amplitude of the input during each period as controlled by clock and timing generator 90. Clock and timing generator 90 coordinates the passing of the peak amplitude signal from peak detector 50 to sample and hold circuit 60. The output of sample and hold circuit 60 is a piecewise linear representation of the peak amplitudes of the acoustic energy emitted from the workpiece. The piecewise linear representation is passed through low pass active filter 70 to smooth the signal prior to passing the smooth signal to output 80 and level detection/flaw alarm 100. Output 80 provides a smooth representation of the peak amplitudes of the acoustic energy emitted from the workpiece properly scaled for recording on a strip chart recorder for later analysis. Level detection/flaw alarm 100 provides an adjustable threshhold and immediate indication of the smooth representation of the peak amplitudes exceeding the predetermined threshhold above which is considered a defect in bonding between laminar layers. Recorder remote start/stop circuit 120 provides for automatically starting and stopping a strip chart recorder during testing. Calibration circuit 110 in conjunction with clock and timing generator 90 provides an input signal to transducer 10 so that gain adjustment can be made resulting in an output signal 80 in a range compatible with the strip chart recorder.

Figure 5:
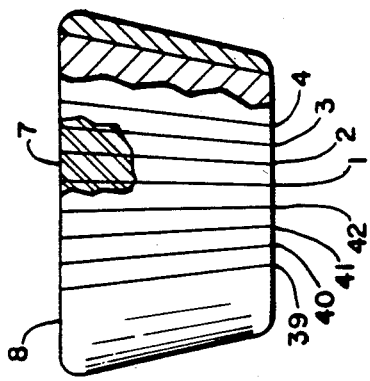
FIG. 5 is a pulverizer roll showing scan lines and indicating an area of defective bonding.

Prior to testing a pulverizer roll for clad disbond, scan lines are marked on the frustrum shaped surface as shown in FIG. 5. The scan lines are approximately equally spaced around the circumference of the pulverizer roll with the spacing greater at the larger diameter end of the frustrum shape of the roll.

Figure 4:
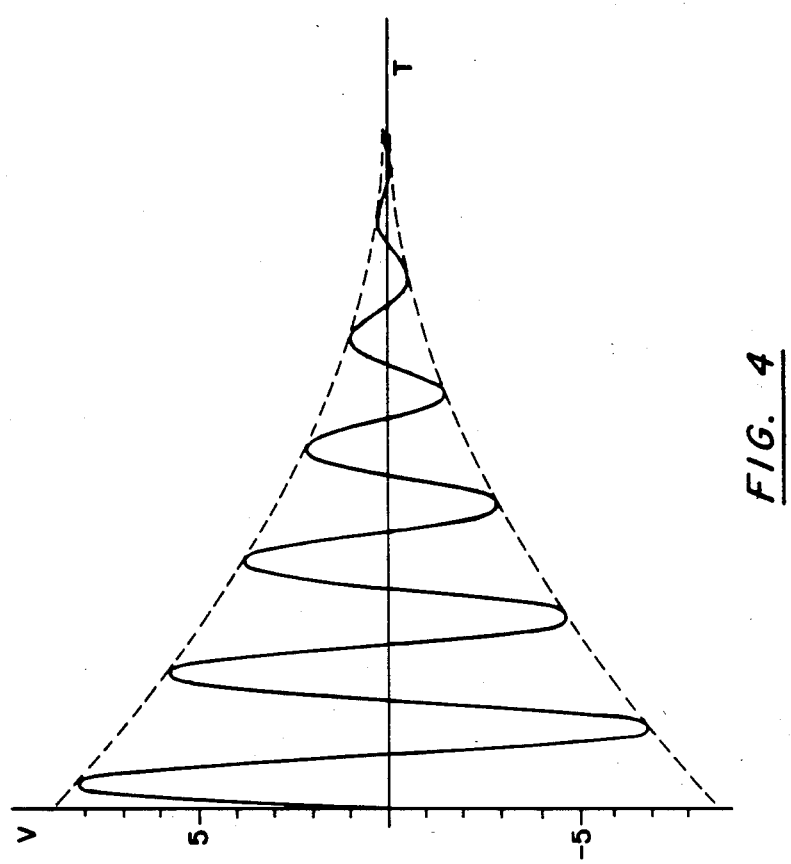
FIG. 4 is a typical acoustic wave emitted from an area of a laminar workpiece with defective bonding between laminar layers.
Figure 3:
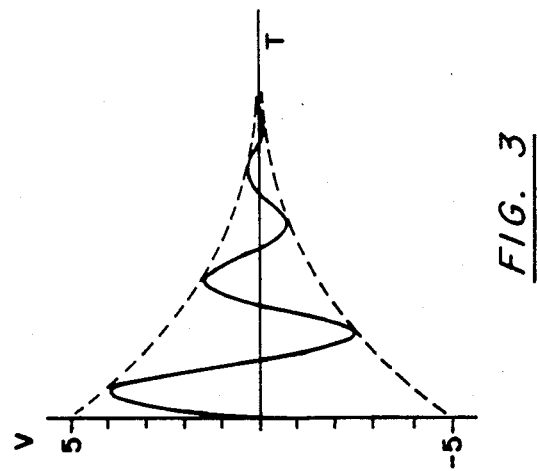
FIG. 3 is a typical acoustic wave emitted from an area of a laminar test workpiece with good bonding between laminar layers.

During clad disbond testing, pulverizer roll 8 is repetitively impacted along each scan line. The repetitive impacts have been accomplished using a pneumatic hammer of the type used to remove welding flux. Each impact imparts energy to the workpiece; the workpiece subsequently reradiates a portion of the imparted energy. The integrity of the bond between a clad layer and a base layer in the region where the energy was imparted to the workpiece can be determined by the amplitude of the energy emitted from the workpiece. A transducer is mounted beneath the pneumatic hammer to receive the energy emitted from the workpiece and for generating a signal representative of the emitted energy for analysis. A typical representation of the energy emitted from the workpiece for a single impact in the region of a good bond is shown in FIG. 3. Typically, such a representation is an exponentially decreasing sinusoid. A typical representation of energy emitted from the workpiece in the region of a defective bond for a single impact is represented in FIG. 4. The representation of the energy emitted from the workpiece in the region of a poor bond between the clad layer and a base material is also an exponentially decreasing sinusoid. However, the initial peak is approximately two times the amplitude of the initial peak of the energy emitted from the workpiece in the region of a good bond.

Figure 2A:
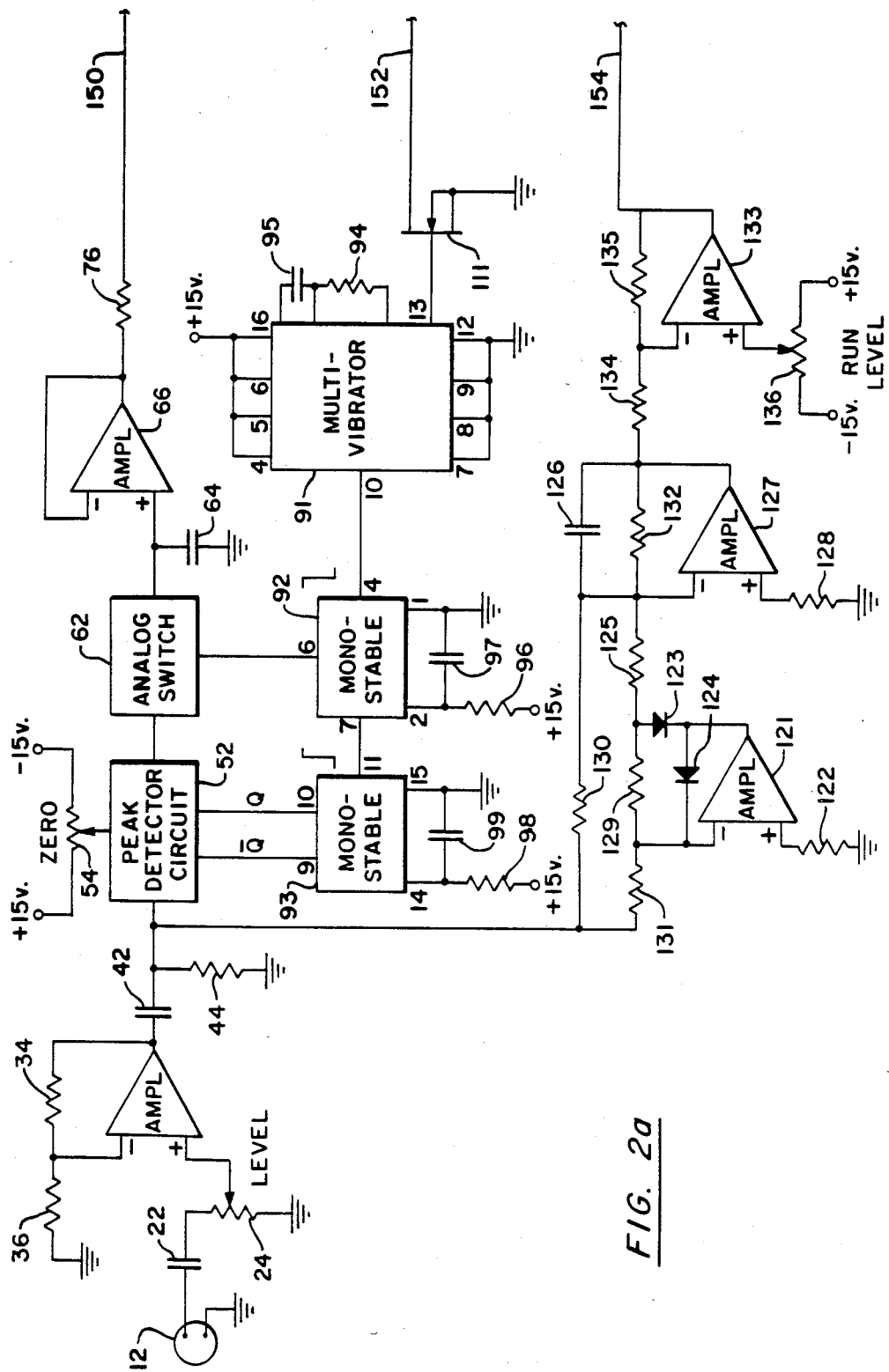
FIGS. 2a and 2b are a circuit diagram of the clad disbond apparatus of FIG. 1 in more detail.
Figure 2B:
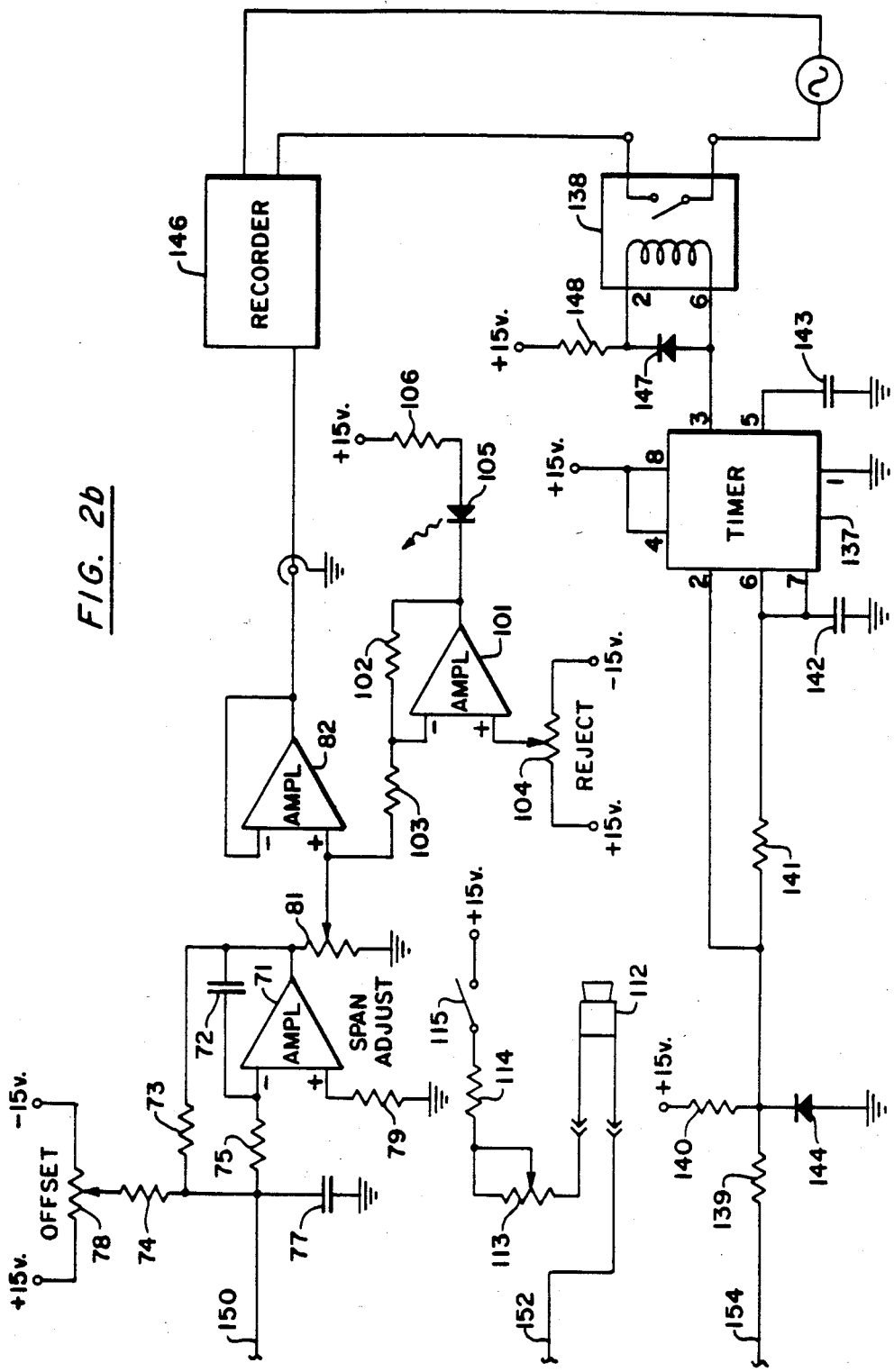
Figure 6:
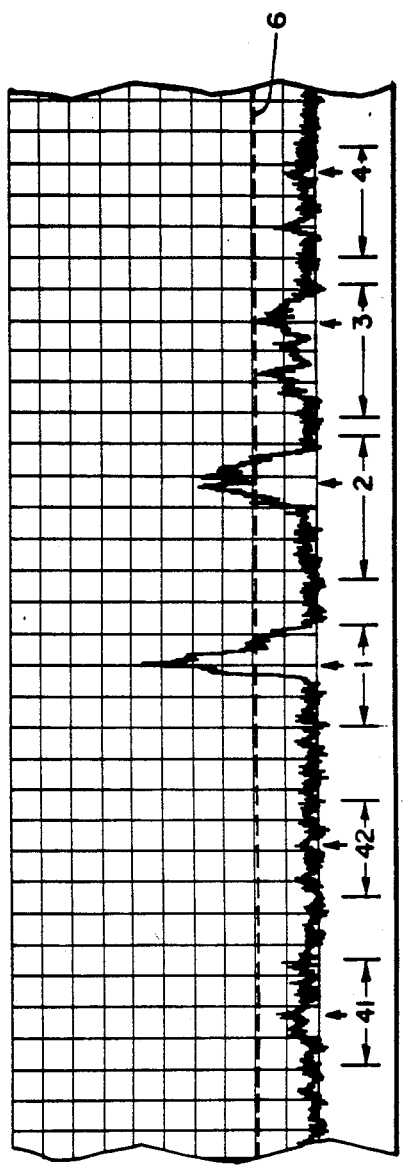
FIG. 6 is a strip chart record of the smooth representation of the peak amplitude of acoustic energy emitted from the pulverizer roll of FIG. 5.

It should be understood that repetitive impacts of the workpiece result in repetitive energy emitted from the workpiece in the form of an exponentially decaying sinusoid of the type shown in FIGS. 3 and 4. This is the signal representative of the energy emitted from the workpiece that is analyzed by the circuits of FIGS. 1 and 2. The smooth representation of the peak amplitude of the acoustic energy emitted from the workpiece is shown in FIG. 6. Each of the scans 41, 42, 1, 2, 3 and 4 that correspond to the scan lines on pulverizer roll 8 of FIG. 5 have been marked. Scanning of pulverizer roll 8 was from the smaller diameter end to the larger diameter end with a scan rate of approximately 3 to 12 inches per second. Thus, the length of strip chart varies from scan to scan. The strip chart record permits remote analysis of clad disbond testing. A horizontal broken line 6 indicates the threshhold of emitted energy above which is considered a defect in clad bonding. The entire scan 41 falls below the threshhold and therefore represents that there is no defective bonding along scan 41. No defective bonding is likewise represented by scan 42. The upper portions of scans 1 and 2 indicate an area of defective bonding between a clad layer and a base layer or the body of pulverizer roll 8. The latter portion of scan 3 indicates the edge of a clad disbond area. Scan 4 represents an area of no defective bonding. A shaded area 7 has been sketched in FIG. 5 to represent the defective bond area determined from the analysis of the strip chart record of FIG. 6. Detecting areas of defective bonding permits these areas to be repaired prior to placing pulverizer roll 8 into service.

Transducer 10 is an electro-acoustical transducer such as microphone 12. Microphone 12 receives the energy emitted from the workpiece being tested and generates a signal representative of the emitted energy.

High pass filter 20 is comprised of capacitor 22, a 0.33 microfarad capacitor, and series potentiometer 24, a 1.5 megaohm resistance. Potentiometer 24 adjusts the level of the signal supplied to amplifier 32 to avoid saturation.

Preamplifier 30 is comprised of amplifier 32, feedback resistor 34, a 470 kilohm resistance, and resistor 36 a 100 kilohm resistance. Preamplifier 30 amplifies the level controlled signal received from high pass filter 20.

Coupling stage 40 is comprised of capacitor 42 a 0.1 microfarad capacitor and resistor 44 and a 1 megaohm resistor. Coupling stage 40 receives the amplified signal from preamplifier 30, blocks any DC component introduced by preamplifier 30 and passes the resulting signal to peak detector 50 and recorder remote start/stop circuit 120.

Peak detector 50 is comprised of peak detecting circuit 52, a specialized amplifier that tracks the analog input signal received from coupling stage 40 until a maximum positive amplitude is reached. The value of the maximum amplitude is held at an analog output available to sample and hold circuit 60 until reset to a user-specified reference voltage determined by the voltage set on potentiometer 54. The voltage across potentiometer 54 ranges from −15 volts to +15 volts with the resulting user-specified reference voltage being near 0 volts. The maximum amplitude value held at the analog output of peak detecting circuit 52 is periodically transferred to sample and hold circuit 60 with the periodic transfer initiated by clock and timing generator 90. Peak detecting circuit 52 is commercially available for example Model 4085 SM manufactured by Burr-Brown.

Sample and hold circuit 60 is comprised of analog switch 62, the closing of which conducts the peak amplitude value from peak detector circuit 52 to capacitor 64, a 0.001 microfarad capacitor where the peak value is maintained until the next subsequent closing of analog switch 62. The closing of analog switch 62 is initiated by clock and timing generator 90 to coordinate resetting the peak value maintained by peak detector circuit 52 to the user-specified reference voltage maintained by potentiometer 54 immediately following transfer of the peak value to capacitor 64 by analog switch 62. Isolation amplifier 66 provides as an output the voltage on capacitor 64 representing the maximum value detected by the sample and hold circuit during the preceding period. Analog switch 62 is a commercially available switch, for example, Model CD 4016A manufactured by Radio Corporation of America.

Clock and timing generator 90 is comprised of multivibrator 91 and dual monostables 92 and 93. Multivibrator 91 provides two functions: the first function in conjunction with monostable 92 and 93 will be discussed here. The second function in conjunction with calibration circuit 110 will be discussed below. Multivibrator 91 is a free running multivibrator providing as an output a square wave, the frequency of which depends upon the external RC network of resistor 94 and capacitor 95. Resistor 94 is a 100 kilohm resistor and capacitor 95 is a 0.1 microfarad capacitor resulting in a frequency that permits peak detecting circuit 52 to track at least the first positive half wave of a representative signal from each of the repetitive impacts on a workpiece. Several positive half cycles may be tracked before transferring the peak value to capacitor 64 and resetting peak detecting circuit 52 to the user-specified reference voltage. Furthermore, the representative signal from several, perhaps as many as three to five, of the repetitive impacts may be tracked before the peak value detected by peak detecting circuit 52 is passed by analog switch 62 to capacitor 64. The manner in which the representative signal of a number of impacts is controlled is by varying the magnitude of the product of the magnitude of resistor 94 and capacitor 95. Multivibrator 91 is commercially available, for example, Model CD 4047A manufactured by Radio Corporation of America.

The output square wave from multivibrator 91 is the input signal to monostable vibrator 92. Monostable vibrator 92 detects the low to high transition of incoming pulses from multivibrator 91 and triggers in response thereto an output pulse, the width of which is dependent upon resistor 96 and capacitor 97, to actuate analog switch 62. Resistor 96 is a 100 kilohm resistor and capacitor 97 is a 0.001 microfarad capacitor.

The complement of the pulse that activates analog switch 62 provides the input to trigger the monostable vibrator 93. Monostable vibrator 93 triggers on a high-to-low transition and generates both a pulse and its complement to reset peak detecting circuit 52 to the user-specified voltage concomitantly with transferring the peak value maintained by peak detection circuit 52 to capacitor 64 via analog switch 62. The RC combination of resistor 98 and capacitor 99 determine the width of the pulse generated by monostable vibrator 93. Resistor 98 is a 100 kilohm resistor and capacitor 99 is a 0.001 microfarad capacitor. Monostable multivibrators are commercially available, for example, Model 4528B manufactured by Fairchild.

Low pass active filter 70 receives at its input the piecewise linear peak amplitude signal as the output of isolation amplifier 66 and provides at its output a smooth representation of the peak amplitude of the acoustic energy emitted from the workpiece. Low pass active filter 70 is comprised of amplifier 71, capacitor 72 a 0.01 microfarad capacitor, resistors 73 and 74 which are 820 kilohm resistors, resistor 75 which is a 330 kilohm resistor, resistor 76 which is an 820 kilohom resistor, capacitor 77 which is a 0.01 microfarad capacitor, and potentiometer 78 which is a 20 kilohm resistor having 30 volts across the terminals ranging from −15 volts to +15 volts. Potentiometer 78 provides an offset adjustment to adjust the zero point of the output, for example, on a strip chart recorder, to compensate for the offset introduced by the users-specified reference voltage of peak detector 50. Output 80 is comprised of potentiometer 81, a 20 kilohm resistor which receives the smooth representation of the peak amplitude of the acoustic energy emitted from the workpiece from amplifier 71 and permits adjustment of the span of the output signal, for example, to be of a convenient amplitude for recording on strip chart recorder 146. The span adjusted signal is the input to isolation amplifier 82 which drives the output device such as strip chart recorder 146.

The span adjusted output signal is also provided to level detection/flaw alarm circuit 100. Level detection/flaw alarm circuit 100 is comprised of comparator 101, resistor 102 a 1.5 megaohm resistor and resistor 103 a 100 kilohm resistor, potentiometer 104, a 20 kilohm resistor with 30 volts across the terminals ranging from −15 to +15 volts, light emitting diode 105 and current limiting resistor 106 a 1.2 kilohm resistance. Resistor 106 limits the current passing through LED 105 to a safe level. LED 105 glows when the junction of LED 105 and comparator 101 is low. This represents the smooth representation of the peak amplitude of the acoustic energy emitted from the workpiece exceeding the reject level set on potentiometer 104. Comparator 339 is commercially available, for example, Model LM 339 manufactured by Signetics.

Multivibrator 91 also provides a square wave input to calibration circuit 110. Power amplifier 111 provides sufficient currrent to drive speaker 112 when the circuit is completed through potentiometer 113, a 50 ohm resistance, resistor 114, a 390 ohm resistance and switch 115. Having operated the clad disbond apparatus and having located a defective bond area 7 as shown in FIG. 5 and having recorded the smooth representation of the peak amplitude of the acoustic energy emitted from the workpiece as shown in FIG. 6, speaker 112 is placed such that acoustic energy emitted from speaker 112 energizes microphone 12 and switch 115 is closed. Potentiometer 113 is adjusted until the same amplitude of response is obtained from calibration circuit 110 as was obtained in locating a defective disbond area. Switch 115 is then opened and the setting on potentiometer 113 remains unchanged. Calibration circuit 110 may be used at a later time to calibrate the clad disbond apparatus without having a pulverizer roll at hand having a known disbond area.

The output signal from coupling stage 40 is also the input signal to recorder remote start/stop circuit 120. The remote start/stop circuit is comprised of an active filter, a comparator, an electronic switch and a relay.

The active rectifier is comprised of amplifier 121, resistor 122, a 10 kilohm resistance, diodes 123 and 124 resistor 125 a 10 kilohm resistance capacitor 126 a 0.22 microfarad capacitance, amplifier 127, resistor 128 a 5 kilohm resistance and resistors 129, 130, 131 and 132 all 20 kilohm resistances. The active rectifier converts the incoming signal to a DC voltage.

The comparator is comprised of comparator 133, resistance 134 a 33 kilohm resistance, resistor 135 a 1 megaohm resistance and potentiometer 136 a 20 kilohm resistance. Potentiometer 136 has 30 volts across the terminals ranging from −15 volts to +15 volts and is used to establish a threshhold signal level which turns the recorder on when the output of comparator 133 goes low.

Timer 137 is used as an electronic switch to energize relay 138 when the output of comparator 133 goes low. Resistors 139, 140 and 141 are all 2.2 kilohm resistances. Capacitor 142 is a 0.22 microfarad capacitor, capacitor 143 is 0.1 microfarad capacitor. Diode 144 serves to maintain the trigger input of timer 137 one diode voltage drop above the ground when the output of comparator 133 is low. When the output of comparator 133 goes low and switch 137 turns on, relay 138 is energized closing switch 145 and in turn energizing recorder 146. Thus, as a scan along one of the scan lines as shown in FIG. 5 is commenced the signal level as monitored by recorder remote start/stop circuit 120 increases turning on recorder 146 to record the smooth representation of the peak amplitudes of the acoustic energy emitted from the workpiece during the scan. Upon completion of a scan the signal level as monitored by recorder remote start/stop 120 decreases, the output of comparator 133 goes high and recorder 146 is turned off to await the commencement of a subsequent scan. When recorder 146 is turned off, energy stored in coil of relay 138 is dissipated through diode 147; resistor 148, a 150 kilohm resistor, limits the in-rush current for relay 138. Switch 137 is commercially available, for example, Model SE555 manufactured by Signetics.

Although the preferred embodiment has been described with respect to detection of clad disbond in pulverizer rolls, it is not limited thereto. The invention has application in detecting clad disbond in metallic workpieces in which one or more layers of clad material is applied over a base material.

We claim:

1. Apparatus for inspecting laminar workpieces for defects in bonding between a clad layer and a base material comprising:

means for impacting a laminar workpiece to impart energy thereto;

a transducer means for receiving energy emitted from the impacted workpiece and for generating a signal representative of the emitted energy;

a peak detecting means for receiving and tracking the signal generated by the transducer means and for producing a signal representative of the peak of the received signal;

a sample and hold means for periodically receiving the detected peak signal from the peak detecting means and producing a piecewise linear output that maintains as an output the last received peak; and a filter means for receiving the piecewise linear output of the sample and hold means and for providing an output that is a smooth representation of the piecewise linear output of the sample and hold means.

2. An apparatus for inspecting laminar workpieces as recited in claim 1 wherein the peak detecting means periodically produces an output that is the peak of the signal generated by the transducer for the preceding period.

3. An apparatus for inspecting laminar workpieces as recited in claim 1 further comprising a high pass filter interposed between the transducer and the peak determining means to receive the signal generated by the transducer means and prevent the DC component of the signal from passing to the peak detector means.

4. An apparatus for inspecting laminar workpieces as recited in claim 3 further comprising a preamplifier to receive the filtered signal from the high pass filter and a coupling stage to receive the amplified signal from the preamplifier and to prevent any DC component introduced into the signal by the preamplifier from passing to the peak detection means.

5. An apparatus for inspecting laminar workpieces as recited in claim 2 further comprising a timing means connected to both the peak detecting means and the sample and hold means for establishing a period during which the signal generated by the transducer is tracked and for coordinating transfer of the peak signal from the peak detecting means to the sample and hold means at the end of the tracking period.

6. An apparatus for inspecting laminar workpieces as recited in claim 5 further comprising a calibration means for simulating energy emitted from the workpiece during calibration of the inspecting apparatus.

7. An apparatus for inspecting laminar workpieces as recited in claim 1 further comprising level detection means by receiving the smooth output from the filter means and for comparing the smooth output to a predetermined threshhold, the level detection means producing as an output an indication of the flaw in the bonding between layers when the smooth output signal from the filter means exeeds the predetermined threshhold.

8. An apparatus for inspecting laminar workpieces as recited in claim 1 further comprising circuit means for receiving the transducer signal and for producing a signal in response thereto to complete an external circuit when the transducer signal exceeds a predetermined value.

9. A method of inspecting laminar workpieces for defects in bonding between layers comprising:

repeatedly imparting energy to the laminar workpiece by repetitive physical impacts;

receiving energy emanated from the workpiece in the region of the impacts in response to the imparted energy and converting the received energy to an electric signal representative of the emanated energy;

tracking the electric signal retaining the maximum value of the electric signal subsequent to the tracking means last being reset;

periodically sampling the retained maximum value of the electrical signal representative of the energy emanated from the workpiece;

periodically resetting the tracking means to a predetermined value subsequent to sampling the retained maximum value;

maintaining a signal representative of the sampled maximum value between periodic samplings resulting in a piecewise linear signal;

filtering the piecewise linear signal;

predetermining a threshold received energy level below which is considered a good bond and above which is considered a defect in bonding; and comparing the filtered piecewise linear signal to the predetermined threshold to ascertain the presence or absence of a defect in bonding between layers, whereby when the filtered piecewise linear signal is greater than the predetermined threshold a defect in bonding exists between layers of the laminar workpiece in the region of the impacts.

* * * * *